United States Patent [19]
Öhman

[11] Patent Number: 6,030,080
[45] Date of Patent: Feb. 29, 2000

[54] DEVICE AND METHOD FOR FILMING A DIMLY ILLUMINATED OBJECT

[75] Inventor: Rolf Öhman, Lund, Sweden

[73] Assignee: Tilly Medical Products AB, Lund, Sweden

[21] Appl. No.: 09/200,601

[22] Filed: Nov. 27, 1998

[30] Foreign Application Priority Data

Nov. 27, 1997 [SE] Sweden ................................. 9704363

[51] Int. Cl.[7] ....................................................... A61B 3/14
[52] U.S. Cl. ............................................................. 351/206
[58] Field of Search ..................... 351/205, 206, 351/221, 246; 348/262, 265, 340, 216, 217

[56] References Cited

U.S. PATENT DOCUMENTS 4,831,452  5/1989  Takanashi et al. ...................... 348/340
5,048,946  9/1991  Sklar et al. .
5,214,503  5/1993  Chiu et al. .
5,225,859  7/1993  Fleischman .............................. 351/206

FOREIGN PATENT DOCUMENTS 0 554 643  8/1993  European Pat. Off. .

*Primary Examiner*—George Manuel
*Attorney, Agent, or Firm*—Browdy and Neimark

[57] ABSTRACT

A device for filming a dimly illuminated object, especially the eye, comprises a source of light for illuminating the object/eye, a light amplifier for amplifying the light reflected from the object/eye, and filming picture recording equipment. The source of light is a source of white light with a low intensity of the emitted light. The device comprises elements for separating at least two of the three primary colors from the reelected light, a light amplifier for amplifying the light for each separated primary color, and filming picture recording equipment for recording the amplified light for each separated primary color. A method for filming the object/eye can be carried out by means of the device.

16 Claims, 1 Drawing Sheet

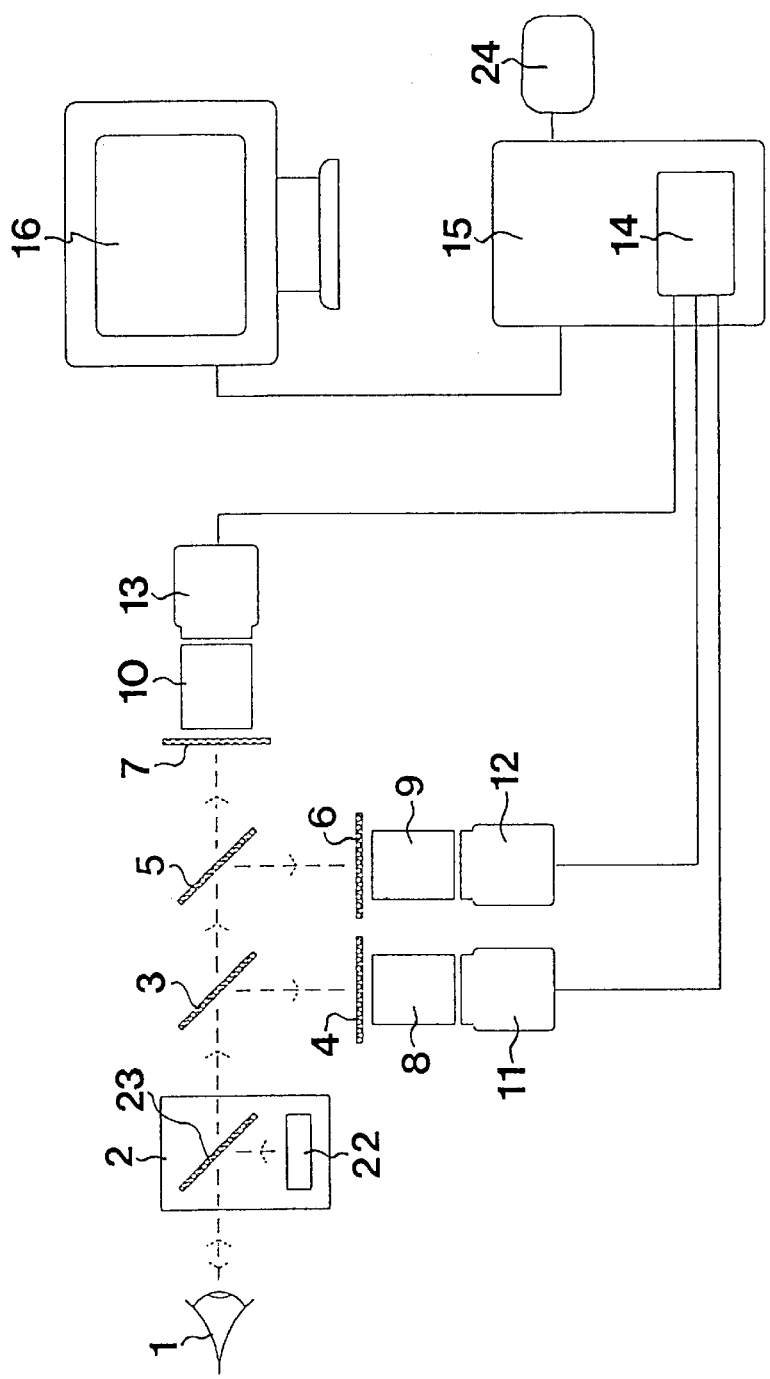
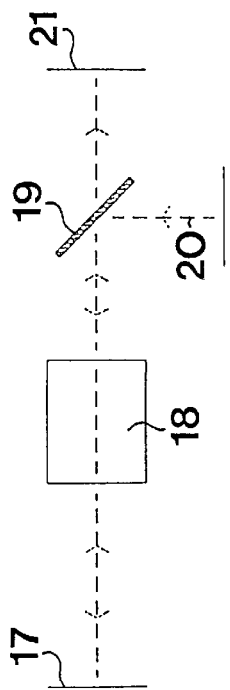
FIG 1
FIG 2

DEVICE AND METHOD FOR FILMING A DIMLY ILLUMINATED OBJECT

FIELD OF THE INVENTION

The present invention relates generally to a device for filming a dimly illuminated object, said device comprising a light amplifier for amplifying the light reflected from the object and reproducing the object on the light amplifier, and picture recording equipment filming the light amplifier's amplified reproduction of the object.

The invention also relates to a method for filming a dimly illuminated object, the light reflected from the object in the form of a reproduction of the object being amplified and the amplified reproduction then being recorded by filming picture recording equipment.

Specifically, the invention concerns such a device and such a method for filming the eye, the device comprising a source of light for illuminating the eye with white light of low intensity.

Although the invention concerns filming of dimly illuminated objects in general, the following description of the background art as well as a preferred embodiment of the invention are restricted to the particular application to the eye.

BACKGROUND ART

There are two basic prior-art techniques of picturing and/or studying different parts of the eye, such as the retina, especially for medicinal purposes.

The first technique is still photography, which is carried out by means of a flashlight emitting white light. This still can be obtained in color thanks to the light emitted by the flashlight being white. By using this technique it is not possible to continuously follow sequences and changes since you are dependent on the charging time of the flashlight.

The second technique is filming, in real time, using infrared light. The reason for using infrared light is that the pupil does not become smaller. Thus, sufficient light intensity for filming is achieved. With infrared light, only the differences in heat or temperature in the pictured object are measured. The drawback of this technique is that the detailed information disappears since there is no difference in heat between small details in the object.

Filming makes it possible to continuously follow sequences and changes. Besides recording a sequence for later analysis, it is of course also possible to observe the sequence as it proceeds.

There is one drawback, however, viz. only such parts of the eye as reflect precisely the incident infrared wavelengths can be seen by using the prior-art technique. This means that all the other information from other parts of the color spectrum is not available.

An example of a similar technique is disclosed in European Patent Application EP 554 643. The light illuminating the eye has a predetermined wavelength and can be produced by a light-emitting diode. A light amplifier amplifies the light reflected in the eye, whereupon a CCD TV camera performs the conversion to a picture, which then constitutes a monochromatic reproduction.

SUMMARY OF THE INVENTION

An object of the present invention is to provide a device, which makes it possible to real-time film a dimly illuminated object in color, especially the eye.

A further object is to provide a method for real-time filming of a dimly illuminated object in color, especially the eye.

Thus the invention makes it possible to directly in real time observe a dimly illuminated object in color, by which is understood reproduction of the object on the basis of the information within at least two different wavelengths or wavelength ranges, each corresponding to a color component, of the light reflected from the object.

An advantage of the invention in the special case of the eye is that it is possible to make a very extensive analysis of a patient's eye in a very short time. All the information is available in each picture and can be obtained by using different types of picture analysis.

BRIEF DESCRIPTION OF THE DRAWINGS

A preferred embodiment of the invention applied to the eye will now be described in more detail with reference to the accompanying drawings, in which FIG. 1 is a schematic view of an embodiment of the inventive device; and FIG. 2 illustrates how the embodiment shown in FIG. 1 of an inventive device can be calibrated in respect of colors.

DESCRIPTION OF A PREFERRED EMBODIMENT

With reference to FIG. 1, a device according to the invention for watching the eye 1 is shown. A source of light 22 emitting white light is arranged to illuminate the eye 1. More specifically, a so-called fundus camera 2 or an equivalent optical instrument is arranged in front of the eye 1. The source of light 22 is in this embodiment arranged in the fundus camera 2, a semi-transparent mirror 23 directing the light to the eye 1 and letting through light reflected from the eye. As is conventional, and as is illustrated in FIG. 1, the light reflected from the optic fundus is imaged along the optical axis of the fundus camera, and the illuminating beam of white light is generally coaxial with the optical axis in the region adjacent the eye.

Fundus cameras are well known in the field and will not be described in more detail here. Here, and in the following claims, "fundus camera" means any optical instrument adapted for viewing or imaging the fundus of the eye.

In the beam path of the light reflected from the eye after the fundus camera 2 there are in this embodiment two means 3, 5 for separating the three primary colors, viz. red, blue and green. The separating means 3, 5 are color reflectors which reflect certain wavelengths and let others through. Since the primary colors are three in number, two separating means are sufficient to divide the light into its primary color components.

For each primary color, a correction filter 4, 6, 7 is arranged for correct color reproduction. After each correction filter a light amplifier 8, 9, 10 and filming picture recording equipment 11, 12, 13 are arranged. In this embodiment each of these pieces of filming picture recording equipment is a video camera and will below be referred to as a video camera. The light amplifier 8, 9, 10 has a photocathode and is known in itself. The light amplification can be in the order of 30,000 times.

Each video camera 11, 12, 13 has an output which is connected to a frame grabber 14, which is a digitizing card for video signals. The digitizing card is arranged in a computer 15, which in turn is connected to a display unit 16, in this case a screen. The computer can also be connected to a storage unit 24 for storing the information for subsequent analysis and examination.

The function of the device in FIG. 1 will now be described. The source of light illuminates the eye with white light. The light is reflected by the eye, or more specifically principally by the fundus of the eye, and passes the semi-transparent mirror 23 of the fundus camera 2. The two separating means 3, 5 divide the reflected light into its primary colors, viz, red, blue and green.

The first separating means 3 is a blue reflector which deflects light with wavelengths of up to (i.e. shorter than) about 460 nm while it lets through light with a longer wavelength. The deflected light passes the correction filter 4 which is blue and lets through light with wavelengths of between about 340 and about 525 nm. The light that has passed the blue correction filter 4 falls on the light amplifier 8 in the form of a reproduction of the eye. The light amplifier 8 amplifies the light about 30,000 times. The amplified light in the form of an amplified reproduction of the eye is passed on to the video camera 11.

The light which has been let through by the first separating means 3 proceeds to the second separating means 5. The second separating means 5 is a red reflector which lets through light with wavelengths in the range of about 360–610 nm. The remaining light is deflected. The deflected light passes a correction filter 6 which is red and lets through light with wavelengths above about 600 nm. The light which has passed the red correction filter 6 falls on the light amplifier 9 and on the video camera 12 in a manner corresponding to that described above for blue light.

The light which has been let through both by the first and by the second separating means 3, 5, i.e. light with wavelengths in the range of about 460–610 nm, proceeds to the correction filter 7 which is green and lets through light with wavelengths in the range of about 520–580 nm. The light which has passed the green correction filter 7 falls on the light amplifier 10 and on the video camera 13 in a manner corresponding to that described above for blue light.

The output signals from the video cameras 11, 12, 13 are transmitted to the digitizing card 14, where they are each digitized separately. A common synchronizing pulse is used to synchronize the video cameras.

From the digitizing card 14 the signals are passed on in the computer 15. The three signals are processed in the computer and then transmitted to the display unit 16, in this case a screen. Alternatively, the digitizing of the signals can already be effected in the respective video cameras 11, 12 and 13, and the digital output signals therefrom are then passed on to the computer for carrying out the desirable picture processing.

It goes without saying that the information can be stored for subsequent analysis and examination.

The video cameras are preferably black-and-white CCD cameras.

The physical properties of the light amplifiers 8, 9, 10 make the color information in the amplified light disappear. Only the intensity information remains. However, by knowing which wavelengths are let through by the correction filters and forwarding this information to the computer, it is possible to recreate the color information.

FIG. 2 shows an installation for color calibration of the inventive device. For color calibration, the eye 1 and the fundus camera 2 are replaced by a picture area 17 which is a plate having a white surface, an optical system 18, a semi-transparent mirror 19, and a source of light 20. The source of light 20 has a known spectral distribution and is arranged in the original position of the source of light 22. One color at a time is calibrated, preferably in the red, green and blue part of the spectrum. The mirror 19 is arranged in the original position of the mirror 23, i.e. in front of the separating means 3 at an angle of 45° to the beam path.

The light from the source of light 20 illuminates by means of the optical system 18 the picture area 17, which reflects all the color components of the illuminating light and, in turn, is reproduced in the picture area 21 of the video camera. The distance between the source of light 20 and the mirror 19 is equal to the distance between the mirror 19 and the picture area 21. The optical system 18 contains prisms, lenses and other optical media, and its function is to focus and adjust the size of the picture of the source of light 20.

FIG. 2 shows for the sake of simplicity one picture area 21 only. If the source of light 20 emits white light having a known spectral distribution, all three colors can, however, be calibrated simultaneously. In that case, the picture areas for all three video cameras are arranged in the position 21.

As an alternative embodiment, the light source 22 and the mirror 23 of the fundus camera can also be used for calibration against the white plate 17. In that case, there are optics corresponding to the optical system 18 in the fundus camera.

The software of the computer comprises routines for automatic calibration of the color reproduction, and the colors being practically correctly reproduced.

To obtain a picture with all colors correctly reproduced, it is of course necessary to use the signals from all three primary colors. Precisely for the reproduction of the eye, the conditions, however, are such that the largest part of the information is to be found in the red signal. A smaller part of the information is available in the green signal, and an extremely small amount of the information is to be found in the blue signal. Thus, a large part of the information can be obtained by using but a combination of e.g. the red and the green signal. It goes without saying that equivalent conditions are applicable in other cases.

The inventive device thus makes it possible to real-time film the eye in color with correct color reproduction also at a low light intensity. Thanks to the division of the light into primary colors with a subsequent light amplification of each color separately, real-time filming in color is possible at a low light intensity.

It will be appreciated that the invention is not limited to the above-described embodiment applied to the eye but can be used in general in a similar manner in respect of an arbitrary object which is dimly illuminated as stated in the appended claims.

What I claim and desire to secure by Letters Patent is:

1. A method for filming a dimly illuminated object, the light reflected from the object in the form of a reproduction of the object being amplified and the amplified reproduction then being recorded by filming picture recording equipment, wherein the reflected light is divided by separation therefrom of at least two color components, the light in each of the separated color components is amplified and recorded separately, and the amplified light in each of the separated color components is recorded separately.

2. A method as claimed in claim 1, wherein the recorded light in each of the separated color components is digitized separately and displayed jointly by a display means and/or stored separately by a storage means for subsequent display.

3. A method as claimed in claim 1 for filming the eye, wherein the eye is illuminated with white light of low intensity.

4. A device for filming an eye, comprising a source of white light with low intensity for illuminating the eye, a light amplifier for amplifying the light reflected from the eye and reproducing the eye on the light amplifier, picture recording equipment filming the light amplifier's amplified reproduction of the eye, said picture recording equipment comprising a digitizing unit or having an output connected to a digitizing unit, means for dividing the light reflected from the eye by separation of at least two color components from the said light, a light amplifier for each of the separated color components for amplifying the light in the respective separate color components, filming picture recording equipment for each of the light amplifiers for recording the light amplified by the respective light amplifier, in the respective color components, and a computer which is connected to a display means and/or a storage means for display and storage, respectively, of a recorded picture sequence.

5. A device as claimed in claim 4, wherein the means for dividing are arranged for separation of a color component for each of the three primary colors red, blue and green.

6. The device according to claim 4, wherein the means for dividing the light comprises a reflector for reflecting wavelengths corresponding to one of the color components and letting the remaining wavelengths through.

7. The device according to claim 4, comprising a correction filter arranged in front of the reflector.

8. A device for filming an eye, comprising a source of white light with low intensity for illuminating the eye, a light amplifier for amplifying the light reflected from the eye and reproducing the eye on the light amplifier, picture recording equipment filming the light amplifier's amplified reproduction of the eye, means for dividing the light reflected from the eye by separation of only a red color component and a green color component from the said light, a light amplifier for each of the separated red and green components for amplifying the light in the respective separate color components, and filming picture-recording equipment for each of the light amplifiers for recording the light amplified by the respective light amplifier, in the respective color components.

9. The device according to claim 8, wherein the means for dividing the light comprises a reflector for reflecting wavelengths corresponding to one of the color components and letting the remaining wavelengths through.

10. The device according to claim 8, comprising a correction filter arranged in front of the reflector.

11. In an optic fundus camera having an optical axis and a source of white light of low intensity adapted to illuminate the fundus of an eye, wherein the white light is generally coaxial with the optical axis in a region adjacent to the eye; the improvement comprising:

at least one color-separating reflector disposed across the optical axis and adapted to deflect one color to a lateral imager further comprising a respective color correction filter, a respective light amplifier receiving light through the filter, and a respective moving-picture recording camera receiving light from the light amplifier; and an axial imager located on the optical axis and further comprising a respective color correction filter, a respective light amplifier receiving light through the filter, and a respective moving-picture recording camera receiving light from the light amplifier;

wherein images from the lateral imager and the axial imager are combinable to form colored moving pictures.

12. The fundus camera according to claim 11, comprising picture recording equipment and a digitizing unit, the picture recording equipment being coupled to the digitizing unit.

13. The fundus camera according to claim 12, comprising a computer coupled to a display means and a memory for display and storage of a recorded picture sequence.

14. The fundus camera according to claim 11, comprising a single color-separating reflector, wherein the single color-separating reflector and the color correction filter associated therewith separate substantially red light, and wherein the color correction filter of the axial imager passes substantially green light, whereby two images in red and green light are used to image the fundus.

15. The fundus camera according to claim 11, comprising two color-separating reflectors, wherein one of the two color-separating reflectors passes blue and shorter wavelengths of the light and another one of the two color-separating reflectors passes red and longer wavelengths of the light, and wherein color correction filters associated with the reflectors pass substantially blue and substantially red light, respectively; and wherein the color correction filter of the axial imager passes green light.

16. The fundus camera according to claim 11, wherein the source of white light comprises a partial reflector disposed across the optical axis to reflect the white light along the optical axis.

* * * * *